United States Patent
Geyer et al.

(12)
(10) Patent No.: US 6,732,473 B2
(45) Date of Patent: May 11, 2004

(54) BURST DELIVERY INSECT CONTROL COIL

(75) Inventors: Jill C. Geyer, Racine, WI (US); Robert R. Emmrich, Racine, WI (US); Brian T. Davis, Burlington, WI (US); Patrick J. McCray, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/184,398

(22) Filed: Jun. 27, 2002

(65) Prior Publication Data

US 2004/0000087 A1 Jan. 1, 2004

(51) Int. Cl.⁷ ............................................. A01M 13/00
(52) U.S. Cl. ......................................... 43/125; 424/411
(58) Field of Search .......................... 43/125, 126, 127, 43/129; 424/40, 411, 417, 421, DIG. 10; 428/906; D22/120, 122

(56) References Cited

U.S. PATENT DOCUMENTS

| | | | |
|---|---|---|---|
| 813,323 A | 2/1906 | Rivers | |
| 827,066 A | 7/1906 | Hapner | |
| 2,224,622 A | 12/1940 | Waples | 167/40 |
| 2,765,579 A | 10/1956 | Gordon | 43/127 |
| 3,754,861 A | 8/1973 | Sadahiro | 21/116 |
| 3,796,002 A | 3/1974 | Katsuda | 43/125 |
| 4,126,958 A | 11/1978 | Yokoyama | 43/127 |
| 4,765,090 A | 8/1988 | Kuan et al. | 43/127 |
| 4,959,925 A | 10/1990 | Nelson et al. | 43/125 |
| D329,679 S | 9/1992 | Klapwald | D22/122 |
| 5,447,713 A | 9/1995 | Elsner et al. | 424/40 |
| 5,657,574 A | 8/1997 | Kandathil et al. | 43/125 |
| 5,948,424 A | 9/1999 | Kandathil et al. | 424/411 |
| 6,061,950 A | 5/2000 | Carey et al. | 43/125 |
| 6,286,248 B1 | 9/2001 | Bryant et al. | 43/125 |
| 6,419,898 B1 * | 7/2002 | Flashinski et al. | 424/40 |

FOREIGN PATENT DOCUMENTS

| | | | | |
|---|---|---|---|---|
| JP | 2001122755 A | * | 5/2001 | A61K/7/46 |
| WO | 02/21915 | | 3/2002 | |

* cited by examiner

Primary Examiner—Charles T. Jordan
Assistant Examiner—Kimberly S. Smith

(57) ABSTRACT

The present invention provides an insect control coil that disperses an initial burst or quick release of a high concentration of insect active ingredient into the environment to provide a fast acting initial dose together with a sensory cue indicative of the release of the active substance. In order to accomplish this, the insect control coil includes a spiral-shaped body composed of a burnable material and having an insect control active substance as an ingredient thereof, a coating on the spiral-shaped body which contains an auxiliary amount of an insect control active substance which provides an auxiliary burst of active substance when burnt, and at least one of either the body or the coating further including a sensory cue indicative of the release of the reactive substance from the coating. The coating may be formed on the tip end of the body, or alternately, may be formed intermittently along the length of the body of the coil.

56 Claims, 2 Drawing Sheets

BURST DELIVERY INSECT CONTROL COIL

BACKGROUND OF THE INVENTION

The present invention relates to burnable insect control delivery devices, and more particularly to an insect control coil such as a mosquito coil.

Insect control coils typically have a spiral-shaped body with is composed of a slowly burnable solid material that contains an insect control active ingredient such as a repellant, an insecticide, or an insect growth regulator that is distributed uniformly throughout the body. When the coil burns, heat vaporizes and disperses the insect control active ingredient.

Insect control coils are well known in the art, and such coils are known to contain various compositions and ingredients. One particular type of coil is shown in U.S. Pat. Nos. 5,657,574 and 5,948,424 which is designed to provide quick coverage for room or other environment that previously was devoid of insect control active ingredient. In these coils, the radially outward tip region has a cross-sectional area that is greater than the cross-sectional area of the inner tail region which results in a dispersion of the insect control active ingredient at a greater rate during initial burning of the coil. Although effective, a consumer using such a coil has no way of knowing or confirming that the coil is providing the fast acting initial dose of active released into the environment, other than, perhaps, the simple observation of the greater size of the end of the coil.

SUMMARY OF THE INVENTION

The present invention provides an insect control coil that disperses an initial burst or quick release of a high concentration of insect control active ingredient into the environment to provide a fast acting initial dose. In order to accomplish this, the insect control coil includes a spiral-shaped body composed of a burnable material having an insect control active substance as an ingredient thereof, and a coating on the spiral-shaped body which contains an auxiliary amount of an insect control active substance which provides an auxiliary burst of active substance when burnt. The coating may be formed on the tip end of the body, or alternately, may be formed intermittently along the length of the body of the coil.

In a second embodiment, the coil also includes a sensory cue indicative of the release of the active substance from the coating. The sensory cue may be a component of either the body of the coil or the coating itself.

The sensory cue is used as an indicator for advising a user that the auxiliary amount of insect control active substance contained in the coating is being released into the environment. The sensory cue may be of various types, but preferably is a visual, audible or aromatic cue. For example, the coating could be a different color from the color of the body of the coil itself, and thus result in a coating that looks different on the coil. Another visual indicator could be the addition of a higher amount of oxidizing agent in the coating so that when the coating burns, it sparkles. Likewise, the coating could be composed of materials which would give off a specific color of smoke, i.e. red, white, black, etc. during the initial burst or release of the active ingredient. An audible cue may comprise a hissing sound or a popping sound. Finally, aromatic cues could comprise a fragrance or other specific odor.

DETAILED DESCRIPTION OF THE PREFERRED EMBODIMENTS

Figure 1:
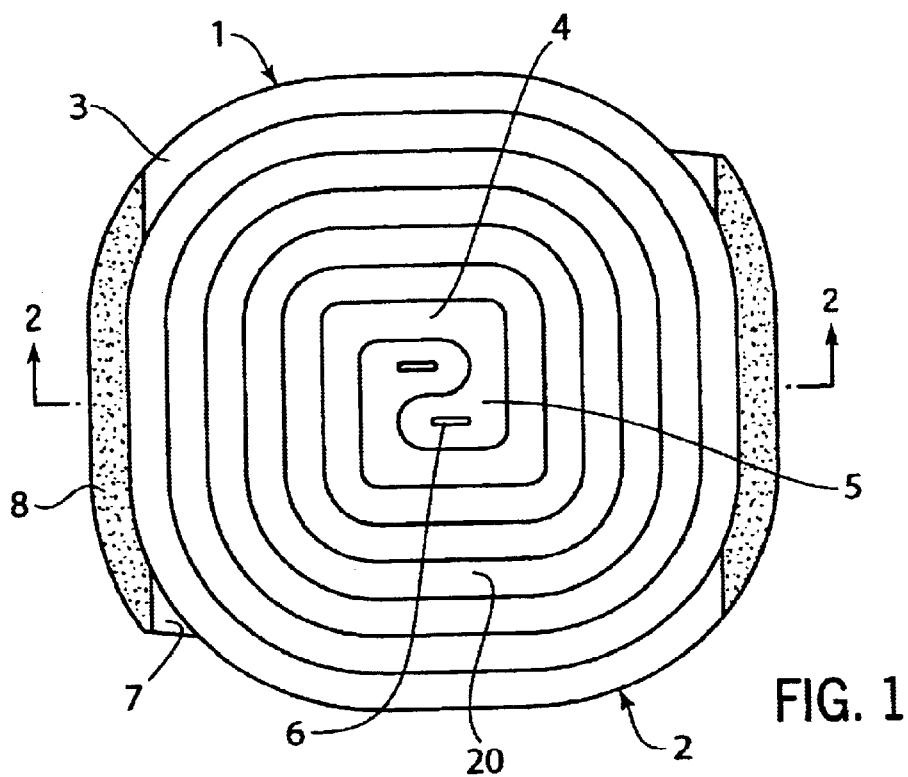
FIG. 1 is a top plan view of a first embodiment of an insect control coil constructed in accordance with the present invention illustrating two coils, which are nested one within the other.
Figure 2:
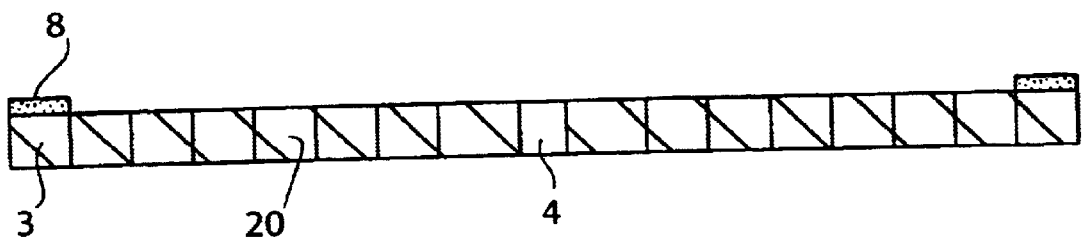
FIG. 2 is a cross-sectional view taken along the plane of the line 2—2 in FIG. 1.
Figure 3:
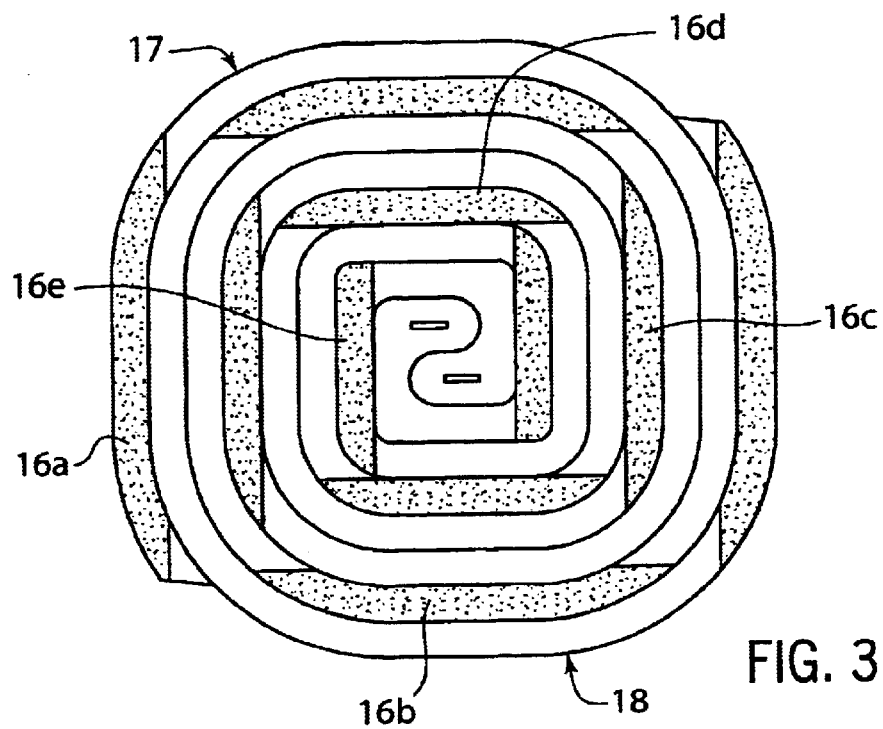
FIG. 3 is a top plan view of a second embodiment of the insect control coil of the present invention also illustrating two coils which are nested one within the other.

Referring now to the drawings, FIGS. 1 and 2 illustrate a first embodiment of the insect control coil of the present invention. In this invention, two insect control coils 1 and 2 respectively, each a spiral in shape, are nested one within the other. As used herein, the term "spiral" or "spiral-shaped" refers to the path of a point in a plane moving around a central point or axis while continuously receding from or approaching that point or axis. The path of the point may be circular, elliptical, oval, rectangular, triangular, or other geometric shape. For example, the coils 1, 2 shown in FIGS. 1 and 3, are substantially square or rectangular in shape.

The coils 1, 2 are manufactured so that they may be separated from each other prior to use, by pulling them apart. Thus, coils 1, 2 are identical and therefore only coil 1 need be described in detail further herein. Coil 1 comprises a spiral-shaped body having an outer tip end 3, an inner tail end 4, and a center section 20. In general, the outer tip end 3 comprises a selected initial portion of the coils 1, 2, measuring from the tip of the coil most remote from the center inwardly for a selected length, while the inner tail end 4 comprises a selected final portion of coils 1, 2, the outer tip end and inner tail, taken together, not encompassing the entire coil. The center section 20 comprises the remaining, middle portion of the length of coils 1, 2. The inner tail end 4 terminates in an enlarged area 5 so as to provide support for a conventional coil stand (not shown) which is received within slot 6 formed therein. As seen best in FIG. 2, coil 1 has a substantially uniform cross-sectional area along its entire length. However, coil 1 could also have a non-uniform cross-sectional area along its length, if desired. In such a circumstance, however, the various regions of coil 1 should smoothly merge into each other without any abrupt changes in size so as to minimize the tendency to crack and/or break during handling.

Preferably, each coil 1, 2 has an outermost ignition section 7 that may (but need not) extend past or beyond a coating 8 and which enables easy lighting of the coil prior to the burning of coating 8. The ignition section 7 is adapted to light readily (as with a match) by means of a reduction of size, the inclusion of conventional oxidants, or the like.

Preferably, the ignition section 7 is tapered to assist in the ignition of the coil 1.

The coils 1, 2 are composed of a burnable base material composed of any well known or conventional combination of ingredients. Representative materials used for the base are wood powder, e.g. saw dust, wood chips, wood fiber, and the like, and various vegetable shell powders, e.g. cocoa shell, peanut shell, and the like which are held together by a binder such as starch, guar gum, and water. However, a wide variety of other conventional and well known slow burning materials can also be used to form the composition of the spiral-shaped body of coil 1. As is well known in the art, various combinations of ingredients may be used to provide a coil which will last for a desired time when burned, i.e. from a few minutes to a few hours.

Coils 1 and 2 are typically used to repel and/or kill flying insects such as mosquitoes which may be present in living quarters or other selected enclosed or open spaces. To this end, coil 1 contains an effective amount of an insect control active ingredient, which is preferably uniformly dispersed throughout the base material of the coil's body, and may be a repellent, an insecticide, or an insect growth regulator. Generally, this effective amount of the insect control active ingredient is from about 0.01% to about 3.0% by weight of coil 1.

Traditionally, pyrethrum or pyrethroid type materials are useful in mosquito coils. Preferred pyrethroids are pyrethrum, resmethrin, bioallethrin, allethrin, and mixtures thereof. A particularly preferred insecticide is allethrin. Other insect control active ingredients can be used such as the repellents citronella, lemon grass oil, lavender oil, cinnamon oil, neem oil, clove oil, sandalwood oil, and geraniol, as well as an insect growth regulator such as hydroprene.

Coils 1 and 2 may also incorporate other burning aids which assist in sustaining the burning of the coil. Traditional and conventional burning aids can be utilized such as sodium and potassium nitrate, and mixtures thereof. Other standard ingredients may be incorporated into the base material of coils 1 and 2, such as dyes, pigments, perfumes, and preservatives.

There are a variety of techniques for manufacturing coils 1 and 2. In one method, the powders are mixed together until uniformly blended whereupon the blend is added to a water/starch mixture to create a dough-like mass. When this dough-like mass is essentially uniform, the insect control active ingredient is blended in until uniformly dispersed therein. The dough is then preferably extruded into a ribbon sheet and cut into the desired coil shape. After the coils are formed, they are then dried by any conventional means such as an oven.

As shown best in FIGS. 1 and 2, coil 1 also includes a coating 8 on the outer or tip end of the spiral-shaped body. In one embodiment, coating 8 contains as one ingredient thereof an auxiliary amount of an insect control active substance which provides an auxiliary burst of active substance when burnt. In other words, when coating 8 burns, it provides an initial burst of a high concentration of insect control active into the environment so as to provide a fast acting initial dose to provide quick coverage of a room or other space with an insect control active ingredient such as a repellent, an insecticide, or an insect growth regulator. The insect control active substance contained in coating 8 may be the same as the active substance dispersed in the body of coil 1, or may be different from the active substance dispersed in the body of coil 1. The composition of coating 8 may or may not be the same as the composition of coil 1. In this regard, coating 8 will contain an auxiliary amount of an active ingredient which may be present in a desired concentration so as to provide the initial burst or quick release of the active into the environment and provide the fast acting initial dose. For example, in one embodiment, the body of coil 1 may contain 20 mg of active ingredient uniformly dispersed therein while the coating may contain 2 mg of an active ingredient. In another embodiment, the body of coil 1 may contain 18 mg of the active ingredient while the coating has 2 mg therein.

Alternatively, the coating 8 may not contain an additional dose of active but, instead, may deliver only the sensory cue effect described below, which cue is made to correlate with or at least signal the presence of an extra dose of active ingredient in the underlying coil 1, 2 itself.

As shown best in FIG. 1, coating 8 is preferably applied only on all or a portion of the tip end 3 of coils 1 and 2. However, as shown in the alternate embodiment of FIG. 3, a coating may also be applied intermittently along the length of coils 1 and 2. With respect to the embodiment shown in FIG. 3, it should be recognized that there are five zones 16a–16e along the length of coils 17 or 18 which comprise the coating. The number of coated zones, the length of the coating of each zone, as well as the distance between each coated zone may be varied, if desired, to vary or correlate with the number of auxiliary "bursts" of active substance, the time duration for each "burst", as well as the time period between each "burst" of insect control active substance. Thus, each coil could contain multiple zones providing multiple auxiliary bursts of the insect control active substance and these zones may be located at any desired location along the length of the coil. As a result, the embodiment shown in FIG. 3 is but one example of the numerous combinations possible.

Figure 4:
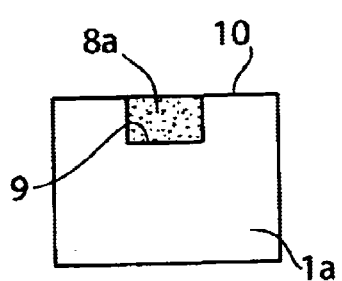
FIG. 4 is a cross-sectional view of a third embodiment of the present invention.

FIG. 4 illustrates a third embodiment where coating 8a is applied to fill a channel 9 formed in the upper surface 10 of coil 1a.

Figure 5:
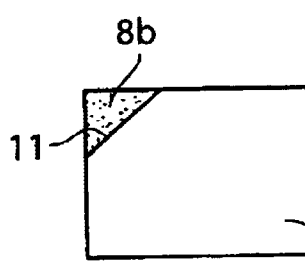
FIG. 5 is a cross-sectional view of a fourth embodiment of the present invention.

FIG. 5 illustrates a fourth embodiment showing coating 8b applied to a chamfered surface 11 along one edge of coil 1b.

Figure 6:
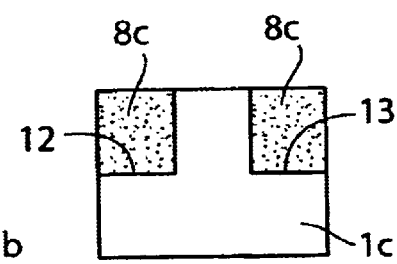
FIG. 6 is a cross-sectional view of a fifth embodiment of the present invention.

FIG. 6 shows a fifth embodiment illustrating coating 8c applied to channels 12 and 13 formed along the top opposite edges of coil 1c.

Figure 7:
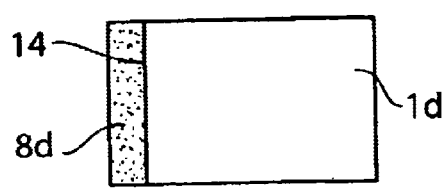
FIG. 7 is a cross-sectional view of a sixth embodiment of the present invention.

FIG. 7 shows a sixth embodiment illustrating coating 8d applied to a side surface 14 of coil 1d.

Figure 8:
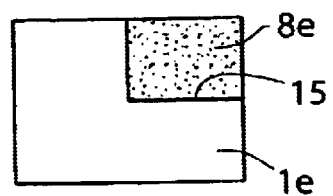
FIG. 8 is a cross-sectional view of a seventh embodiment of the present invention.

FIG. 8 shows a seventh embodiment illustrating coating 8e applied to a channel 15 formed along one top edge of coil 1e.

The coating may be applied in any conventional manner to one or more surfaces of the coil. For example, typical techniques include spraying, using a roller, or extrusion. Also, although FIGS. 1–8 illustrate a rectangular cross section for the body of coil, it should be recognized that it may be square, circular, triangular, oval, elliptical, hexagonal, or any other geometric configuration desired.

In addition to providing an initial burst of a high concentration of insect control active, the coil of the present invention also provides a sensory cue to a user which is indicative of the release of the active substance from the coating. This sensory cue may be formed as part of either the body of the coil, or as part of the composition of the coating. In any event, the sensory cue comprises a visual cue, an audible cue, or an aromatic cue. For example, typical visual cues might the comprise coating being a different color than the body of the coil itself. Likewise, that portion of the body of coil beneath or adjacent the coating might also be a different color than the coating itself. Another visual cue could be the addition of a slightly higher amount of an oxidizing agent such as sodium or potassium nitrate in the composition of the coating. For example, it is known that a composition containing about 12% potassium nitrate will provide a slow burn composition. However, if the amount of potassium nitrate is increased to 25%, the composition will be considered a "fast" burn so that as the composition burns, it sparkles. Yet another visual cue might comprise adding ingredients to the coating which could give off a specific color of smoke, i.e. red, white, black, green, etc. as the coating burns. Examples of audible cues comprise incorporating specific oxidizing agents into the composition of the coating so that as it burns, a hissing sound emanates therefrom. Likewise, one could incorporate ingredients or agents which would result in a popping sound as the coating burns. Finally, an example of an aromatic cue might comprise a specific fragrance or other specific odor which is dispersed into the environment as the coating burns. Preferably, the sensory cue is only incorporated in the coating so that as the coating burns it provides an indicator to the user that a "burst" of auxiliary active insect control ingredient is being released by the coil. However, as indicated previously, the sensory cue may alternately be incorporated in the body of the coil itself if desired, to indicate when the coating is being burnt and the auxiliary active ingredient is being released into the environment.

In any event, coating 8 may be so formulated as to burn quickly compared to the underlying coil 1. In that event, the coating 8 will burn off, providing its burst of active and/or sensory cue, while the rest of the coil 1 burns at a slower, more conventional rate. Alternatively, the coating 8 may be so formulated as to ignite when the burn line of the coil 1 reaches it, causing the coating to burn at a rate fast than the underlying coil for a time, until the coating self-extinguishes. The coating 8 then re-ignites only when the burn line of the coil 1 advances to reach the unburned portion of the coating, this pattern of coating ignition, self-extinguishing, and re-ignition repeating as desired.

EXAMPLE

The objective of this Example is to determine if there are differences between coils treated with a fast burning tip containing active and a coil without a treated tip. The tip treatment has Pynamin Forte (at 0.50%) as the active in the formula. The non-treated coils are blank (6147P65-2) and SCJ China coils at 0.20% Pynamin Forte (6147P65-3).

This "tip treatment" was prepared as a paste-like formulation that is applied starting at the coil tip to about 4–6 cm total in length. It is in that form so that when first lit, it will provide an audible/visible cue that is providing "fast action", burning just ahead of the burning ember of the coil.

Samples

SCJ China Coil—#6147P65-3 containing 0.20% Pynamin Forte

Blank Coil—#6147P65-2 containing no active ingredient (CTOT coil)

Blank Coil—#6147P65-2 with coating containing 0.50% Pynamin Forte applied to the tip (ca. 6 cm).

Coating at the tip of the coil contains:

| Raw Material Name | % (by weight) |
|---|---|
| Starch | 6.00 |
| Sawdust | 5.00 |
| Potassium Nitrate | 17.00 |
| Guar Gum | 0.50 |
| Pynamin Forte | 0.50 |
| Triton X-193 | 0.50 |
| Sodium Benzoate | 0.25 |
| Water | 70.25 |
| | 100.00 |

The amounts of coating applied to each of the 3 coils tested were: For #1=595 mg (3.0 mg Pynamin Forte), #2=632.7 mg (3.2 mg Pynamin Forte), and #6=552.1 mg (2.8 Pynamin Forte). The coating on Coil #1 only burned ca. ⅓ of the way and burned out, while both Coil #2 and Coil #6 burned ca. ⅔ of the way and burned out.

Method Specifics

Three 0.42 cubic meter glass chambers were used to evaluate knockdown in a free-flying mosquito knockdown test using female *Aedes aegypti*. The continuous exposure methodology was followed. Three replicates were conducted for each sample. In addition, control (no treatment) replicates were conducted to monitor potential chamber contamination.

Test Method

Modified Knockdown Test Using Small Glass Chamber (0.42 Cubic Meters)

Three 0.42 cubic meter (0.75 m×0.75 m×0.75 m) glass chambers were used to conduct a knockdown evaluation of free-flying, female *Aedes aegypti*. Ten mosquitoes were released into the chamber and allowed to acclimate for 3 minutes. The coil, lit just outside the chamber, was then placed in the center of the chamber for a continuous exposure test. Knockdown counts were taken at 30-second intervals until 100% knockdown was sustained for 2 consecutive counts or a 10-minute time limit was reached. The mosquitoes were picked up and discarded; no 24-hour mortality counts were taken.

Results

TABLE 1

Mean KT50 and KT80 Values:
Free-Flying Aedes aegypti in 0.42 Cubic
Meter Glass Chamber Continuous Exposure

| | Time in Minutes to % Knockdown of Mosquitoes | |
|---|---|---|
| Treatment | Mean KT50 (S.D.) | Mean KT80 (S.D.) |
| SCJ China Coil | 4.2 (0.25) | 4.9 (0.14) |
| Blank (no A.I.) Coil | NA | NA |
| Blank (no A.I.) Coil with Tip Treatment of Pynamin Forte | 2.3 (0.41) | 2.8 (0.24) |

*KT50 and KT80 values were calculated for each replicate using linear interpolation. Means and standard deviations were then calculated based on 3 replicates per treatment.
NA means knockdown never reached 50% or 80%.

TABLE 2

Free-Flying Mosquito Knockdown Test in 0.42M³
Chamber Using Female Aedes aegypti (ca. 10) Continuous Exposure Mean % Knockdown of Mosquitoes
Time in Minutes

| Treatment | 0.5 | 1.0 | 1.5 | 2.0 | 2.5 | 3.0 | 3.5 | 4.0 | 4.5 | 5.0 |
|---|---|---|---|---|---|---|---|---|---|---|
| SCJ China Coil | 0 | 0 | 0 | 3 | 3 | 13 | 27 | 43 | 60 | 83 |
| Blank (no A.I.) Coil | 0 | 0 | 0 | 0 | 0 | 0 | 0 | 0 | 0 | 0 |
| Blank (no A.I.) Coil with Tip Treatment of Pynamin Forte | 0 | 0 | 10 | 40 | 60 | 94 | 100 | 100 | 100 | 100 |

| Treatment | 5.5 | 6.0 | 6.5 | 7.0 | 7.5 | 8.0 | 8.5 | 9.0 | 9.5 | 10.0 |
|---|---|---|---|---|---|---|---|---|---|---|
| SCJ China Coil | 90 | 93 | 97 | 100 | 100 | 100 | 100 | 100 | 100 | 100 |
| Blank (no A.I.) Coil | 0 | 0 | 0 | 0 | 0 | 0 | 0 | 0 | 0 | 0 |
| Blank (no A.I.) Coil with Tip Treatment of Pynamin Forte | 100 | 100 | 100 | 100 | 100 | 100 | 100 | 100 | 100 | 100 |

Three replicates were conducted for each sample. Test was terminated when 100% knockdown was sustained for 2 consecutive counts. It was assumed that knockdown would not have changed during the remainder of the test and the remaining counts were entered as 100%.

TABLE 3

Control Data.
Mean % Knockdown of Mosquitoes (Based on 3 Replicates)

| | 5 minutes | 10 minutes | 15 minutes | 20 minutes |
|---|---|---|---|---|
| Control (No Treatment) | 0 | 0 | 0 | 0 |

Summary

The blank coil with the tip treatment produced faster knockdown than the SCJ China coil. Therefore Pynamin Forte is being released from the tip treatment coating when burning. The blank coil without the tip treatment produced no knockdown.

We claim:

1. An insect control coil, comprising:
   a spiral-shaped body having an outer tip end and an inner tail end, said body composed of a burnable material and having an insect control active substance as an ingredient thereof;
   a coating on said spiral-shaped body, said coating delivering a sensory cue when burned to correlate with an auxiliary burst of active substance delivered from the coil; and
   wherein a channel is formed in the body and the coating substantially fills and is confined to the channel.

2. The insect control coil of claim 1, wherein the coating contains an auxiliary amount of an insect control active substance that provides an auxiliary burst of active substance when burnt.

3. The insect control coil of claim 2, wherein the active substance in said body is the same as the active substance in said coating.

4. The insect control coil of claim 2, wherein the active substance in said body is different from the active substance in said coating.

5. The insect control coil of claim 1, wherein said tip end has an outermost ignition section that extends past said coating to enable lighting of said body prior to burning of said coating.

6. An insect control coil, comprising:
   a spiral-shaped body having an outer tip end and an inner tail end, said body composed of a burnable material and having an insect control active substance as an ingredient thereof;
   a coating on said spiral-shaped body, said coating delivering a sensory cue when burned to correlate with an a burst of active substance delivered from the coil; and
   wherein the body includes a chamfer formed in an edge of the body, and the coating is applied to the chamfer.

7. The insect control coil of claim 6, wherein the coating contains an auxiliary amount of an insect control active substance that provides an auxiliary burst of active substance when burnt.

8. The insect control coil of claim 7, wherein the active substance in said body is the same as the active substance in said coating.

9. The insect control coil of claim 7, wherein the active substance in said body is different from the active substance in said coating.

10. The insect control coil of claim 6, wherein said tip end has an outermost ignition section that extends past said coating to enable lighting of said body prior to burning of said coating.

11. An insect control coil, comprising:
    a spiral-shaped body having an outer tip end and an inner tail end, said body composed of a burnable material and having an insect control active substance as an ingredient thereof;
    a coating on said spiral-shaped body, said coating delivering a sensory cue when burned to correlate with an auxiliary burst of active substance delivered from the coil; and
    wherein the coating is applied only to a side surface of the body.

12. The insect control coil of claim 11, wherein the coating contains an auxiliary amount of an insect control active substance that provides an auxiliary burst of active substance when burnt.

13. The insect control coil of claim 12, wherein the active substance in said body is the same as the active substance in said coating.

14. The insect control coil of claim 12, wherein the active substance in said body is different from the active substance in said coating.

15. The insect control coil of claim 11, wherein said tip end has an outermost ignition section that extends past said coating to enable lighting of said body prior to burning of said coating.

16. An insect control coil, comprising:
   a spiral-shaped body having an outer tip end and an inner tail end, said body composed of a burnable material and having an insect control active substance as an ingredient thereof;
   a coating on said spiral-shaped body, said coating delivering a sensory cue when burned to correlate with an auxiliary burst of active substance delivered from the coil; and
   wherein a channel is formed in an edge of the body, and the coating is applied to the channel.

17. The insect control coil of claim 16, wherein the coating contains an auxiliary amount of an insect control active substance that provides an auxiliary burst of active substance when burnt.

18. The insect control coil of claim 17, wherein the active substance in said body is the same as the active substance in said coating.

19. The insect control coil of claim 17, wherein the active substance in said body is different from the active substance in said coating.

20. The insect control coil of claim 16, wherein said tip end has an outermost ignition section that extends past said coating to enable lighting of said body prior to burning of said coating.

21. An insect control coil, comprising:
   a spiral-shaped body having an outer tip end and an inner tail end, said body composed of a burnable material and having an insect control active substance as an ingredient thereof;
   a coating on said spiral-shaped body, said coating containing an auxiliary amount of an insect control active substance which provides an auxiliary burst of active substance when burnt;
   at least one of either said body or said coating further including a sensory cue indicative of the release of said active substance from said coating; and
   wherein said sensory cue comprises a visual cue, and said visual cue comprises colored smoke.

22. The insect control coil of claim 21, wherein the active substance in said body is the same as the active substance in said coating.

23. The insect control coil of claim 21, wherein the active substance in said body is different from the active substance in said coating.

24. The insect control coil of claim 21, wherein said tip end has an outermost ignition section that extends past said coating to enable lighting of said body prior to burning of said coating.

25. The insect control coil of claim 21, wherein said coating is located on the tip end of said body.

26. The insect control coil of claim 21, wherein said coating is formed intermittently along the length of said body.

27. An insect control coil, comprising:
   a spiral-shaped body having an outer tip end and an inner tail end, said body composed of a burnable material and having an insect control active substance as an ingredient thereof;
   a coating on said spiral-shaped body, said coating containing an auxiliary amount of an insect control active substance which provides an auxiliary burst of active substance when burnt;
   at least one of either said body or said coating further including a sensory cue indicative of the release of said active substance from said coating; and
   wherein said sensory cue comprises a visual cue, and said visual cue comprises sparkling.

28. The insect control coil of claim 27, wherein the active substance in said body is the same as the active substance in said coating.

29. The insect control coil of claim 27, wherein the active substance in said body is different from the active substance in said coating.

30. The insect control coil of claim 27, wherein said tip end has an outermost ignition section that extends past said coating to enable lighting of said body prior to burning of said coating.

31. The insect control coil of claim 27, wherein said coating is located on the tip end of said body.

32. The insect control coil of claim 27, wherein said coating is formed intermittently along the length of said body.

33. An insect control coil, comprising:
   a spiral-shaped body having an outer tip end and an inner tail end, said body composed of a burnable material and having an insect control active substance as an ingredient thereof;
   a coating on said spiral-shaped body, said coating containing an auxiliary amount of an insect control active substance which provides an auxiliary burst of active substance when burnt;
   at least one of either said body or said coating further including a sensory cue indicative of the release of said active substance from said coating; and
   wherein said sensory cue comprises a visual cue, and said visual cue comprises said coating being a different color than said body.

34. The insect control coil of claim 33, wherein the active substance in said body is the same as the active substance in said coating.

35. The insect control coil of claim 33, wherein the active substance in said body is different from the active substance in said coating.

36. The insect control coil of claim 33, wherein said tip end has an outermost ignition section that extends past said coating to enable lighting of said body prior to burning of said coating.

37. The insect control coil of claim 33, wherein said coating is located on the tip end of said body.

38. The insect control coil of claim 33, wherein said coating is formed intermittently along the length of said body.

39. An insect control coil, comprising:
   a spiral-shaped body having an outer tip end and an inner tail end, said body composed of a burnable material and having an insect control active substance as an ingredient thereof,
   a coating on said spiral-shaped body, said coating containing an auxiliary amount of an insect control active substance which provides an auxiliary burst of active substance when burnt;
   at least one of either said body or said coating further including a sensory cue indicative of the release of said active substance from said coating; and
   wherein said sensory cue comprises an audible cue, and said audible cue comprises a hissing sound.

40. The insect control coil of claim 39, wherein the active substance in said body is the same as the active substance in said coating.

41. The insect control coil of claim 39, wherein the active substance in said body is different from the active substance in said coating.

42. The insect control coil of claim 39, wherein said tip end has an outermost ignition section that extends past said coating to enable lighting of said body prior to burning of said coating.

43. The insect control coil of claim 39, wherein said coating is located on the tip end of said body.

44. The insect control coil of claim 39, wherein said coating is formed intermittently along the length of said body.

45. An insect control coil, comprising:
 a spiral-shaped body having an outer tip end and an inner tail end, said body composed of a burnable material and having an insect control active substance as an ingredient thereof;
 a coating on said spiral-shaped body, said coating containing an auxiliary amount of an insect control active substance which provides an auxiliary burst of active substance when burnt;
 at least one of either said body or said coating further including a sensory cue indicative of the release of said active substance from said coating; and
 wherein said sensory cue comprises an audible cue, and said audible cue comprises a popping sound.

46. The insect control coil of claim 45, wherein the active substance in said body is the same as the active substance in said coating.

47. The insect control coil of claim 45, wherein the active substance in said body is different from the active substance in said coating.

48. The insect control coil of claim 45, wherein said tip end has an outermost ignition section that extends past said coating to enable lighting of said body prior to burning of said coating.

49. The insect control coil of claim 45, wherein said coating is located on the tip end of said body.

50. The insect control coil of claim 45, wherein said coating is formed intermittently along the length of said body.

51. An insect control coil, comprising:
 a spiral-shaped body having an outer tip end and an inner tail end, said body composed of a burnable material and having an insect control active substance as an ingredient thereof;
 a coating on said spiral-shaped body, said coating containing an auxiliary amount of an insect control active substance which provides an auxiliary burst of active substance when burnt;
 at least one of either said body or said coating further including a sensory cue indicative of the release of said active substance from said coating; and
 wherein said sensory cue comprises an aromatic cue, and said aromatic cue comprises a fragrance.

52. The insect control coil of claim 51, wherein the active substance in said body is the same as the active substance in said coating.

53. The insect control coil of claim 51, wherein the active substance in said body is different from the active substance in said coating.

54. The insect control coil of claim 51, wherein said tip end has an outermost ignition section that extends past said coating to enable lighting of said body prior to burning of said coating.

55. The insect control coil of claim 51, wherein said coating is located on the tip end of said body.

56. The insect control coil of claim 51, wherein said coating is formed intermittently along the length of said body.

* * * * *

UNITED STATES PATENT AND TRADEMARK OFFICE
CERTIFICATE OF CORRECTION

PATENT NO.    : 6,732,473 B2
DATED         : May 11, 2004
INVENTOR(S)   : Jill C. Geyer et al.

It is certified that error appears in the above-identified patent and that said Letters Patent is hereby corrected as shown below:

<u>Column 8,</u>
Line 29, replace "a" with -- auxiliary --

Signed and Sealed this

Third Day of May, 2005

JON W. DUDAS
*Director of the United States Patent and Trademark Office*